US005195375A

United States Patent [19]

Tenerz et al.

[11] Patent Number: 5,195,375

[45] Date of Patent: Mar. 23, 1993

[54] MINIATURIZED PRESSURE SENSOR

[75] Inventors: Lars Tenerz, Upsala; Bertil Hök, Västerås, both of Sweden

[73] Assignee: Radi Medical Systems AB, Upsala, Sweden

[21] Appl. No.: 721,508

[22] PCT Filed: Jan. 12, 1990

[86] PCT No.: PCT/SE90/00027

§ 371 Date: Jul. 11, 1991

§ 102(e) Date: Jul. 11, 1991

[87] PCT Pub. No.: WO90/07906

PCT Pub. Date: Jul. 26, 1990

[30] Foreign Application Priority Data

Jan. 13, 1989 [SE] Sweden ........ 8900121

[51] Int. Cl.[5] ........ G01D 5/30; G01L 7/08; G01L 9/00

[52] U.S. Cl. ........ 73/705; 73/862.624; 128/667; 128/675; 250/231.19

[58] Field of Search ........ 73/705, 862.48, 862.624; 250/227.21, 231.19; 128/667, 675, 748

[56] References Cited

U.S. PATENT DOCUMENTS

| | | | |
|---|---|---|---|
| 3,789,667 | 2/1974 | Porter et al. | 73/406 |
| 4,543,961 | 10/1985 | Brown | 128/667 |
| 4,548,205 | 10/1985 | Armeniades et al. | 128/748 |
| 4,611,600 | 9/1986 | Cohen | 128/667 |
| 4,711,246 | 12/1987 | Alderson | 128/667 |
| 4,712,566 | 12/1987 | Hok | 128/748 |
| 4,727,730 | 3/1988 | Boiarski et al. | 128/667 |
| 4,936,310 | 6/1990 | Engstrom et al. | 128/673 |
| 4,991,590 | 2/1991 | Shi | 73/705 |
| 5,018,529 | 5/1991 | Tenerz et al. | 128/667 |
| 5,085,223 | 2/1992 | Lars et al. | 128/675 |

FOREIGN PATENT DOCUMENTS

| | | |
|---|---|---|
| 441725 | 11/1985 | Sweden . |
| 8602836-2 | 2/1988 | Sweden . |

OTHER PUBLICATIONS

"Silicon Microcavities Fabricated with a New Technique," Reprinted from *Electronics Letters*, May 22, 1986, vol. 22, No. 11, pp. 615–616.

*Primary Examiner*—Donald O. Woodiel

*Attorney, Agent, or Firm*—Foley & Lardner

[57] ABSTRACT

A miniaturized pressure sensor for physiological in situ measurements has an elastic material shell having an outer surface with an opening extending therethrough. The opening is covered by an elastic diaphragm and a light conductor having an end surface is disposed inside the shell and connected thereto by a glue joint. A body of silicon or gallium is disposed inside the shell and has a thin, cantilevered, short beam portion and a reflecting surface connected to and perpendicularly projecting from a free end of the short beam portion. The reflecting surface is proximate to the end surface of the light conductor so that when the diaphragm is subjected to a pressure differential, it is forced to move thereby causing a corresponding movement of the short beam portion so that the reflecting surface is positioned opposite to the end surface of the light conductor.

11 Claims, 2 Drawing Sheets

MINIATURIZED PRESSURE SENSOR

BACKGROUND OF THE INVENTION

1. Field of the Invention

The present invention relates to a miniaturized pressure sensor with a shell of an elastic material, an elastic diaphragm arranged over an opening situated in the surface of the shell, a light conductor arranged inside the shell, a silicon body arranged inside the shell and a reflecting surface arranged on the body such as to be opposite of the light conductor.

2. Description of the Related Art

A device of the kind mentioned above is known from Swedish patent specification 86 02836-2. There is still a need to further miniatures this known pressure transducer, but in attempting to do so problems occur which are directly related to the small dimensions.

The known pressure transducer is a so-called relative pressure transducer, which means that it measures the pressure difference between ambient pressure and a reference pressure. The reference pressure is in contact with the atmospheric pressure via an air duct inside the shell. This air duct has a constriction formed by a silicon body situated in the region of the diaphragm.

The problem with the known pressure transducer is that the resistance of the air duct to volume changes caused by the diaphragm moving is not sufficiently low, and for rapid pressure changes this leads to the occurrence of a certain excess pressure in the distal air volume nearest the diaphragm, this air volume being limited on one side by the constriction. This excess pressure falsifies the measuring result.

SUMMARY OF THE INVENTION

The present invention has the object of providing a miniaturized pressure sensor of the kind described above, which allows maintenance of atmospheric pressure in the distal air volume nearest the diaphragm in spite of the diaphragm moving quickly.

Another object of the invention is to achieve a pressure sensor of the kind described above, and which has reduced compliance. Compliance is herein defined as volume change per pressure change. In other words, a small deflection or movement of the diaphragm shall provide a small volume change. This can be accomplished by either reducing the deflection or the size of the diaphragm.

In accordance with the invention, the above-mentioned objects are achieved by a body comprising a thin, cantilevering, short beamlike structure of silicon arranged for actuation by the diaphragm, and by the reflecting surface being arranged at the free end of the cantilever part of the beam structure, and upstanding from it, such that the pressure changes acting on the diaphragm will move the beam structure and thereby the reflecting surface, which then will move in front of the end of the light conductor or optical fiber.

By making the beam structure short, in accordance with the invention, and thereby decreasing the deflection of the diaphragm for an applied pressure, an acceptable signal-to-noise ratio is retained, while at the same time the pressure sensor has great sensitivity to rapid pressure changes.

By reducing the opening over which the diaphragm is arranged, in accordance with the invention, and thereby the volume change per pressure change, there is obtained the advantage that the diaphragm will be stiffer and afford good protection for the sensor. However, there is an adhesion effect resulting in the tendency for the diaphragm to stick to the beam structure when the structure moves. This gives rise to an undesired hysteresis in the pressure measuring result.

In accordance with another embodiment of the invention, the adhesion effect associated with a reduced opening is avoided by the cantilevering beam structure having a hump on its back part situated under the diaphragm, this hump projecting into the opening in the shell surface of the sensor.

BRIEF DESCRIPTION OF THE DRAWINGS

Two embodiments of the invention will now be described in more detail with reference to the accompanying drawings, wherein.

DETAILED DESCRIPTION OF THE PREFERRED EMBODIMENT

Figure 1:
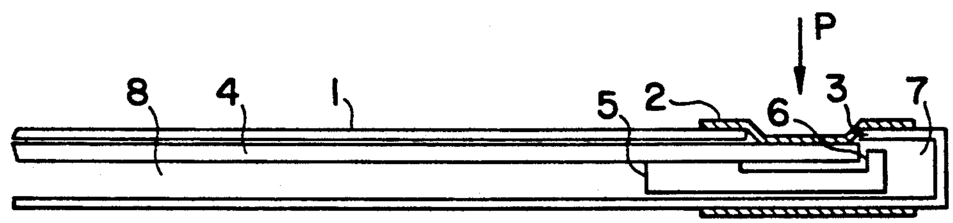
FIG. 1 illustrates a miniaturized pressure sensor according to the state of the art as appears in the above-mentioned Swedish patent.

The known pressure sensor includes a shell 1 of elastic material, and an elastic diaphragm 2 arranged over an opening 3 situated in the shell surface. A light conductor 4 and a silicon body 5 are arranged inside the shell. A reflecting surface 6 is arranged opposite the end surface of the light conductor 4. The amount of reflected light in the light conductor 4 is responsive to the amount with which the ambient pressure P deflects the diaphragm 2 and thereby the end surface of the light conductor or optical fiber 4 in relation to the reflecting surface 6. As will be seen from FIG. 1, the silicon body 5 forms a constriction between the air volume 7 at the distal end of the diaphragm and the air duct 8 inside the proximal part of the shell. This constriction is a disadvantage in miniaturization. In addition, it is different from one sensor to the next, due to reasons concerned with manufacturing techniques.

Figure 2:
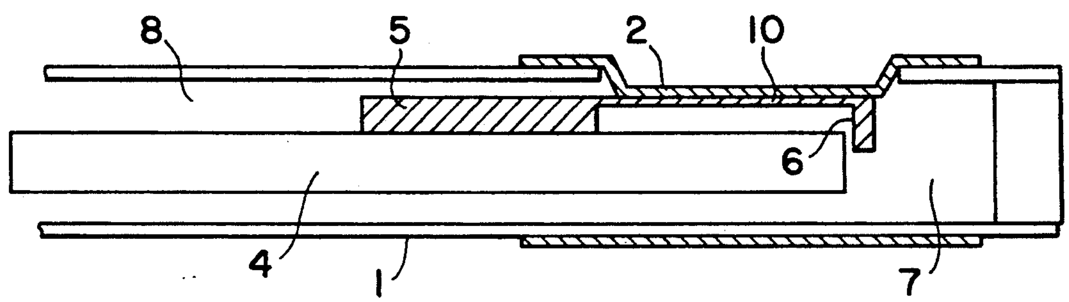
FIG. 2 is a cross-sectional view of a miniaturized pressure sensor in accordance with the present invention.

FIG. 2 illustrates the pressure sensor in accordance with the present invention. The silicon body 5 is provided with a thin, cantilevering, short beam structure 10 arranged for actuation by the diaphragm 2. The structure is produced from single crystalline silicon by anisotropic etching of the 100-plane or the 111-plane, which have a lower etching rate than surrounding crystal planes. A vertical mirror can be etched in this way at the end of the beam structure By selective etching, the thickness of the beam can be defined within the area of magnitude from about 5 to about 30 μm. By using single crystalline silicon the beam structure is provided with extremely good bending properties, and since it can have the mentioned thickness its length can be made less than the length of the free end of the optical fiber in the embodiment according to FIG. 1. The length of the complete sensor can thus be reduced in this way.

The silicon body 5 is cemented to the light conductors or optical fiber 4, which is in turn cemented to the shell 1.

Selective etching means that the etching rate is dependent on doping. The silicon can be p-doped or p-doped silicon can be n-doped. Different etching liquids can be used, inter alia postassium hydroxide.

Figure 3:
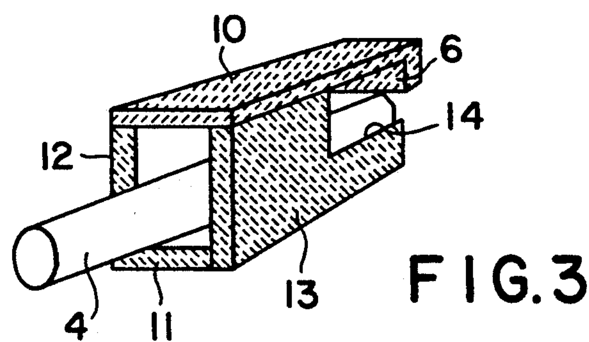
FIG. 3 is a perspective view of an assembly means for ensuring a free path for the volume of air deciding reference pressure.

The silicon body illustrated in FIG. 3 is used to provide a well-defined air duct and for facilitating assembly of the optical fiber in the sensor. The body 5 is substantially quadratic in cross section and is formed partly by the beam structure 10, which is provided at its end with the reflecting surface 6, and partly by an upwardly open elongate box with a bottom wall 11 and two side walls 12, 13. The two side walls are each provided with an upwardly open cutaway part, of which only one, 14, is shown. These parts 14 only extend a short distance along the length of the side walls, this distance corresponding to the length of the cantilevering part of the beam structure 10.

The beam structure is joined to the box by an atomic bonding process (see Tenerz, Hök, Electronic Letters, May 22, 1986, Vol. 22, No. 11, pages 615-616) or anodic bonding by depositing a glass layer in the joint.

When the sensor is assembled, the box 10-13 is inserted in the shell 1 upon to the position corresponding to the one in FIG. 2, the beam structure then being fixed to the shell, e.g. by cementing, or in some other way. The light conductor or optical fiber is then inserted in the end opening of the box in the manner illustrated in FIG. 3. The position of the fiber relative the reflecting surface is easy to determine with great precision since the bottom, side and roof walls of the box serve as guides. It will be understood that the air duct mentioned above is formed between the optical fiber and the four walls 10-13. These walls are smooth and have well defined sizes, in comparison with the rather random constrictions which can occur in the embodiment according to FIG. 1 in connection with the body 5 being cemented in the shell. Although not described in more detail above, the side walls 12, 13 and bottom wall are either made from flat wafers which are joined to each other, or the walls 11, 12 and 13 are made integral using such a selective etching procedure of the kind mentioned above.

Figure 4:
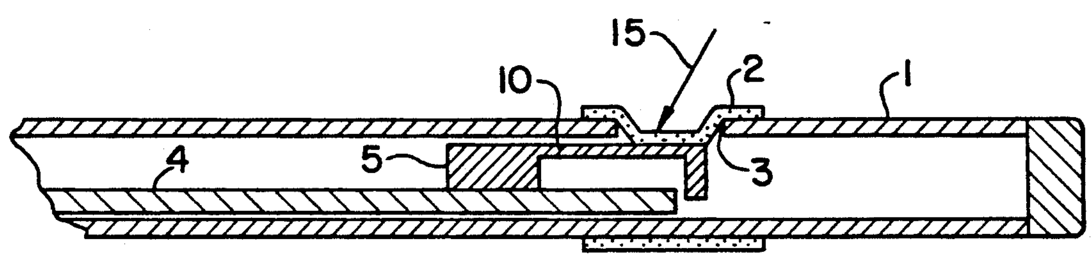
FIG. 4 is a cross-sectional view of a miniaturized pressure sensor having a reduced area of an opening for a diaphragm.

FIG. 4 illustrates a miniaturized pressure sensor similar to the one in FIG. 2. In the embodiment according to FIG. 4, the area of the opening 3 has been reduced in relation to the one in FIG. 2, with the object of increasing the compliance of the sensor. This embodiment further affords the advantages that the diaphragm 2 will be stiffer compared with the one of FIG. 2, and therefore provide good mechanical protection to the sensor. However, there is a disadvantage that an adhesion effect occurs, i.e. The diaphragm tends to stick to the beam structure 5 in the region denoted by the arrow 15. This falsifies the measuring result.

Figure 5:
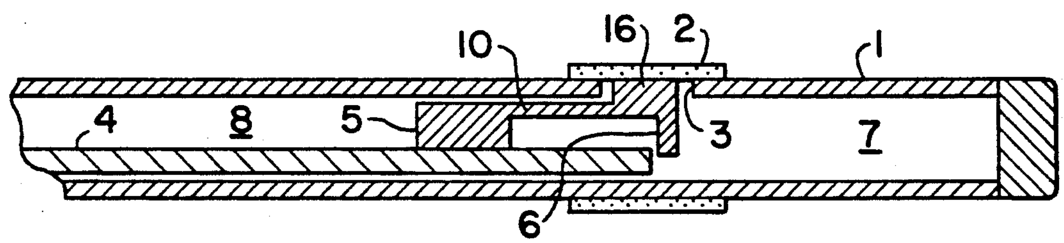
FIG. 5 is a cross-sectional view of a miniaturized pressure sensor in accordance with a second embodiment of the present invention.

FIG. 5 illustrates a miniaturized pressure sensor in accordance with a second preferred embodiment of the invention. Here as well, the opening 3 for the diaphragm 2 has a reduced area compared with the embodiment in FIG. 2. Here, the diaphragm is substantially flat and does not bulge down into the opening as in FIG. 2. The beam structure 10 of the body 5 has a hump 16 on its back part in the region of the latter situated under the opening 3, this hump projecting into the opening 3 such as to be in contact with the diaphragm 2. This configuration results in that the adhesion effect no longer occurs or is at least considerably reduced. The upper surface of the hump is flat and its contour, seen from above in relation to FIG. 5 is somewhat less than the contour of the opening so that the hump does not jam in the wall of the opening 3 when the beam structure moves. The hump 16 is preferably made integral with the body and is preferably produced simultaneously with the beam structure 10 by selective etching of the silicon as described above.

This embodiment of the body 5 can also have the form of a box similar to the one with open end walls, as illustrated in FIG. 3, the beam structure 10 being provided with the hump 16 on its back.

It should be noted that in all the embodiments of the invention described above the beam structure 10 is only in contact with the diaphragm 2, and is not cemented to the diaphragm.

The above described embodiments of the invention can be modified in many ways and varied within the scope of the inventive concept.

We claim:

1. A miniaturized pressure sensor for physiological in situ measurements, comprising:

an elastic material shell having an outer surface with an opening extending therethrough;

an elastic diaphragm covering said opening;

a light conductor having an end surface being disposed inside said shell and being connected to said shell by a glue joint; and a body of silicon or gallium arsenide having a thin, cantilevered, short beam portion and a reflecting surface connected to and perpendicularly projecting from a free end of said short beam portion such that said reflecting surface is proximate to said end surface of said light conductor, said body being glued to said light conductor and being disposed inside said shell;

wherein when said diaphragm is subjected to a pressure differential it is forced to move causing a corresponding movement in said short beam portion such that said reflecting surface is positioned opposite to said end surface of said light conductor.

2. A miniaturized pressure sensor as claimed in claim 1, wherein said short beam portion has a hump thereon which projects into said opening.

3. A miniaturized pressure sensor as claimed in claim 1, wherein said body includes a through opening for receiving said light conductor.

4. A miniaturized pressure sensor as claimed in claim 3, wherein said body is disposed in said shell so that a first air volume is created in said shell in front of said body and a second air volume is created in said shell behind said body, and said light conductor is received in said body so that an air duct is formed between said first and second air volumes.

5. A miniaturized pressure sensor as claimed in claim 4, wherein said body is cemented to the inside of said shell.

6. A miniaturized pressure sensor as recited in claim 5, wherein an exterior diameter of said shell at a distal part of said sensor is less than 0.5 mm.

7. A miniaturized pressure sensor as claimed in claim 1, wherein said body is made from silicon and said short beam portion is formed by selective etching of a single crystalline silicon in the 100-plane or the 111-plane.

8. A miniaturized pressure sensor as claimed in claim 7, wherein said short beam portion has a thickness within a range of approximately 5 to 30 μm and a length within a range of approximately 0.3–0.6 mm.

9. A miniaturized pressure sensor as recited in claim 1, wherein said body has a substantially quadratic cross-section.

10. A miniaturized pressure sensor as recited in claim 9, wherein said body is formed as an elongated box having a top wall, a bottom wall and a pair of side walls, said top wall including said short beam portion, and said side and bottom walls each being a flat silicon wafer, and wherein each of said pair of side walls has an upwardly extending open cutaway portion which extends a distance along the longitudinal length of said pair of side walls, said distance corresponding to the length of the short beam portion.

11. A miniaturized pressure sensor as recited in claim 10, wherein said top wall is joined to said elongated box by atomic or anodic bonding.

* * * * *